United States Patent [19]

Bergeron, Jr.

[11] Patent Number: 5,843,959

[45] Date of Patent: Dec. 1, 1998

[54] METHODS AND BICYCLIC POLYAMINE COMPOSITIONS FOR THE TREATMENT OF INFLAMMATION

[75] Inventor: Raymond J. Bergeron, Jr., Gainesville, Fla.

[73] Assignee: University of Florida Research Foundation, Inc., Gainesville, Fla.

[21] Appl. No.: 820,027

[22] Filed: Mar. 19, 1997

[51] Int. Cl.$^6$ .......................... A61K 31/445; A61K 31/33; A61K 31/55; A61K 31/40

[52] U.S. Cl. .......................... 514/316; 514/183; 514/212; 514/326; 514/422

[58] Field of Search .................................. 514/316, 326, 514/212, 183, 422

[56] References Cited

FOREIGN PATENT DOCUMENTS

96/28425 9/1996 WIPO .

OTHER PUBLICATIONS

Bergeron et al, Journal of Medicinal Chemistry, vol. 39, No. 13, pp. 2461–2471, 1996.

*Primary Examiner*—William R. A. Jarvis

*Attorney, Agent, or Firm*—Kerkam, Stowell, Kondracki & Clarke, P.C.; Dennis P. Clarke

[57] ABSTRACT

Methods for treating inflammatory conditions wherein the active agent is a polyamine having the formula set forth below:

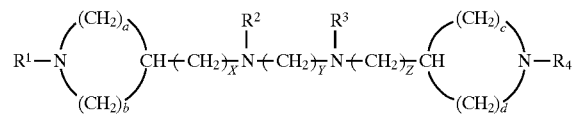

or a salt thereof with a pharmaceutically acceptable acid wherein:

$R_1$, $R_2$, $R_3$ and $R_4$ may be the same or different and represent H, straight- or branched-chain alkyl, aryl, aryl alkyl or cycloalkyl of 1–12 carbon atoms;

a, b, c and d may be the same or different and are integers from 0 to 8, except that when a or c is zero, b or d is greater than or equal to 3 and when a or c is one, b or d is greater than or equal to 2; and X, Y and Z may be the same or different; X and Z are integers from 0 to 10; and Y is an integer from 1 to 10, excluding the polyamine of the formula wherein a=b=c=d=2, X=Z=2 and Y=4.

4 Claims, 8 Drawing Sheets

METHODS AND BICYCLIC POLYAMINE COMPOSITIONS FOR THE TREATMENT OF INFLAMMATION

BACKGROUND OF THE INVENTION

RELATED APPLICATIONS

The active agents employed in the methods and compositions of the invention, as well as methods for their preparation, are described in U.S. patent application Ser. No. 08/080,692 filed Jun. 22, 1993, the entire contents and disclosures of this application being incorporated herein by reference.

FIELD OF THE INVENTION

The present invention relates to novel methods and pharmaceutical compositions for the treatment of inflammation in humans and non-human mammals.

THE STATE OF THE ART

Inflammatory diseases are a widespread cause of human suffering and loss of function. Additionally, the treatment of patients with these diseases represents a very large expense in terms of money, facilities and personnel. The incidence of many such diseases is expected to rise in the future as life expectancy and the median age of the population continue to increase.

Inflammatory diseases are known which affect many diverse tissues and organs in the body. Examples of diseases in which the inflammation is most apparent in the joints and related connective tissue are osteoarthritis, rheumatoid arthritis, tendinitis, bursitis and the like. Osteoarthritis is a progressive disorder of unknown cause that principally affects the hands and large weight-bearing joints and is clinically characterized by pain, deformity and limitation of motion. Pathologically, it is characterized by erosive lesions, cartilage destruction, subchondral sclerosis, cyst formation and osteophytes at the joint margins. Arthritis is a potentially crippling disease that is second only to cardiovascular diseases in producing severe chronic disability [Epstein, *New England Journal of Medicine*, Vol. 239, page 1322 (1989)]. It affects nearly 10% of the population over age 60. This high incidence rate results in billions of dollars in costs annually for medications, surgery and lost productivity [Peyron, *Clin. Orthop.*, Vol. 213, page 13 (1986) and Holbrook, *Am. Acad. Orthopaedic Surgeons*, Vol. 1 (1984)]. These diseases are most often treated with non-steroidal anti-inflammatory agents such as aspirin, ibuprofen and piroxicam, or with anti-inflammatory glucocorticosteroids. However, these treatments suffer either from a lack of efficacy in completely controlling the disease process or from unacceptable toxic side effects.

Rheumatoid arthritis, also called chronic rheumatism, in particular, is a chronic multiple arthritis characterized by inflammatory changes in the synovial membrane of the articular capsule inner layer. Arthritic diseases like rheumatoid arthritis are progressive and cause joint disorders such as deformation and acampsia, often resulting in severe physical disorders due to lack of effective treatment or subsequent deterioration.

Traditionally, these forms of arthritis have been chemotherapeutically treated with various agents, including steroids such as cortisone and other adrenocortical hormones; non-steroidal anti-inflammatory agents such as aspirin, piroxicam and indomethacin; gold agents such as aurothiomalate; anti-rheumatic agents such as chloroquine preparations and D-penicillamine; anti-gout agents such as colchicine; and immuno-suppressors such as cyclophosphamide, azathioprine, methotrexate and levamisole.

However, these drugs have drawbacks such as severe adverse reactions, adverse reactions hampering the drugs' long-term use, lack of sufficient efficacy and a failure to be effective against already-occurring arthritis.

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDS) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including ulcers, that limit their therapeutic potential. An alternative to NSAIDs is the use of corticosteroids, such as prednisone, which have even more drastic side effects, especially when long-term therapy is involved.

Accordingly, there is a need for the development of novel compositions and methods that are useful for the treatment of arthritis and other inflammatory conditions.

Relevant Literature

1. Lovaas, *Med. Hypotheses*, Vol. 45, No. 1, "Hypothesis: Spermine May Be An Important Epidermal Anti-oxidant," pages 59–67 (July 1995)

2. Miles et al, *Free Radical Res.*, Vol. 23, No. 4, "Effects of Superoxide on Nitric Oxide-Dependent N-Nitrosation Reactions," pages 379–390 (October 1995)

3. Esposito et al, *J. Neurochem.*, Vol. 65, No. 1, "Neurokinin Receptors Could Be Differentiated By Their Capacity To Respond To The Transglutaminase-Synthesized Gamma-(glutamyl-5)spermine Derivative Of Substance P," pages 420–426 (July 1995)

4. Purcell et al, *Neurochem. Res.*, Vol. 20, No. 5, "Mast Cells In Neuroimmune Function: Neurotoxicological and Neuropharmacological Perspectives," pages 521–532 (May 1995)

5. Fike et al, *Int. J. Radiation Oncol. Biol. Phys.*, Vol. 32, No. 4, "Cellular Proliferation and Infiltration Following Interstitial Irradiation of Normal Dog Brain is Altered by an Inhibitor of Polyamine Synthesis," pages 1035–1045 (July 1995)

6. Narita et al, *Proc. Natl. Acad. Sci. USA*, Vol. 92, No. 10, "L-arginine May Mediate the Therapeutic Effects of Low Protein Diets," pages 4552–4556 (May 1995)

7. Walters et al, *J. Leukoc. Biol.*, Vol. 57, No. 2, "An Inhibitor of Polyamine Biosynthesis Impairs Human Polymorphonuclear Leukocyte Priming by Tumor Necrosis Factor Alpha," pages 282–286 (February 1995)

8. Tjandrawinata et al, *J. Immunol.*, Vol. 152, No. 6, "Regulation of Putrescine Export in Lipopolysaccharide or IFN-gamma-activated Murine Monocytic-leukemic RAW 264 Cells," pages 3039–3052

9. Ginsburg et al, *Inflammation*, Vol. 17, No. 3, "Killing of Endothelial Cells and Release of Arachidonic Acid. Synergistic Effects Among Hydrogen Peroxide, Membrane-Damaging Agents, Cationic Substances, and Proteinases and Their Modulation By Inhibitors," pages 295–319 (June 1993)

10. Persico et al, *Peptides*, Vol. 13, No. 1, "Substance P Inactivation By Transglutaminase In Vitro," pages 151–154 (Jan.–Feb. 1992)

11. Wickstrom, *Acta Ophthalmol. Copenh.*, Vol. 70, No. 4, "Polyamine and Histopathological Changes After Unilateral Endotoxin-Induced Uveitis and its Contralateral Effects," pages 506–514 (August 1992)

12. Vesela et al, *Pharmacol. Res.*, Vol. 25, No. 4, "Lack of Inhibition of Ornithine Decarboxylase Activity by Ibuprofen," pages 347–352 (May–June 1992)

13. Wickstrom et al, *Ophthalmic Res.*, Vol. 24, No. 3, "Aqueous Humor Polyamines and Alkaline Phosphatase Activity in Endotoxin-Induced Uveitis: Correlations to Diverse Leukocyte Subsets," pages 175–180 (1992)

14. Pacitti et al, *Surgery*, Vol. 112, No. 2, "Stimulation of Hepatocyte System y(+)-mediated L-arginine Transport by an Inflammatory Agent," pages 403–411 (August 1992)

15. Lovaas et al, *Free Radical Biol. Med.*, Vol. 11, No. 5, "Spermine: An Anti-Oxidant and Anti-Inflammatory Agent," pages 455–461 (1991)

16. Wickstrom, *Curr. Eye Res.*, Vol. 10, No. 5, "Polyamines in Rabbit Aqueous Humor After Surgical Trauma to the Eye," pages 463–469 (May 1991)

17. Serniak et al, *Urol. Nefrol. Mosk.*, No. 4, "Diagnostika Urosepsisa," [The Diagnosis of Urosepsis], pages 9–13 (July–August 1990) (Russian language document)

18. Azuma et al, *Gifu. Shika Gakkai Zasshi.*, Vol. 17, No. 2, "Possible Mechanisms of the Anti-Inflammatory Action of Polyamines," pages 509–515 (December 1990) (Japanese language document)

19. Maita et al, *Endod. Dent. Traumatol.*, Vol. 6, No. 5, "Polyamine Analysis of Infected Root Canal Contents Related to Clinical Symptoms," pages 213–217 (October 1990)

20. Ferrante et al, *Clin. Exp. Immunol.*, Vol. 80, No. 3, "Polyamine Oxidase Activity in Rheumatoid Arthritis Synovial Fluid," pages 373–375 (June 1990)

21. Elsayed et al, *Toxicol. Appl. Pharmacol.*, Vol. 102, No. 1, "Effects of Ozone Inhalation on Polyamine Metabolism and Tritiated Thymidine Incorporation into DNA of Rat Lungs," pages 1–8 (January 1990)

22. Colombatto et al, *Agents Actions*, Vol. 24, Nos. 3–4, "Polyamines in Rat Liver During Experimental Inflammation," pages 326–330 (July 1988)

23. Dempsey et al, *Life Sci.*, Vol. 42, No. 20, "Bone Marrow Derived Macrophages Have Polyamine and Ectoenzyme Phenotypes Distinct from Resident Macrophages," pages 2019–2027 (1988)

24. Talal et al, *J. Autoimmun.*, Vol. 1, No. 4, "Rheumatoid Arthritis: An Editorial Perspective Based on Cytokine Imbalance," pages 309–317 (August 1988)

25. Giao et al, *C. R. Acad. Sci. III*, Vol. 307, No. 5, "Mecanisme Epigenetique de la Promotion Tumorale. Interrelation Entre L'inflammation et L'activite D'ornithine Decarboxylase Induites In Vitro Par Le Cancerogene 12-O-Tetradecanoyl-Phorbol-13-Acetate," [Epigenetic Mechanism of Tumor Promotion. Interrelationship Between Inflammation and Ornithine Decarboxylase Activity Induced In Vitro by the Carcinogenic 12-O-Tetradecanoyl-Phorbol-13-Acetate], pages 229–234 (1988) (French language document)

26. Talal et al, *Scand. J. Rheumatol. Suppl.*, Vol. 76, "Abnormalities of T Cell Activation in the Rheumatoid Synovium Detected with Monoclonal Antibodies to CD3," pages 175–182 (1988)

27. Kafy et al, *Agents Actions*, Vol. 24, Nos. 1–2, "Antioxidant Effects of Exogenous Polyamines in Damage of Lysosomes Inflicted by Xanthine Oxidase or Stimulated Polymorphonuclear Leucocytes," pages 145–151 (June 1988)

28. Delcros et al, *C. R. Acad. Sci. III*, Vol. 305, No. 12, "Mise en Evidence de Polyamines Liees a des Proteines Plasmatiques lors de la Croissance Tumorale," [Demonstration of Polyamines Bound to Plasma Proteins During Tumor Growth], pages 465–470 (1987)

29. Lamster et al, *Arch. Oral Biol.*, Vol. 32, No. 5, "The Polyamines Putrescine, Spermidine and Spermine in Human Gingival Crevicular Fluid," pages 329–333 (1987)

30. Delcros et al, *FEBS Lett.*, Vol. 220, No. 1, "Protein-Bound Polyamines in the Plasma of Mice Grafted with the Lewis Lung Carcinoma," pages 236–242 (August 1987)

31. Kanof et al, *J. Pediatr. Gastroenterol. Nutr.*, Vol. 6, No. 1, "Congenital Diarrhea with Intestinal Inflammation and Epithelial Immaturity," pages 141–146 (January–February 1987)

32. Kafy et al, *Agents Actions*, Vol. 18, Nos. 5–6, "In Vitro Interactions Between Endogenous Polyamines and Superoxide Anion," pages 555–559 (August 1986)

33. Oyanagui et al, *Agents Actions*, Vol. 17, Nos. 3–4, "Vasoregulin, a Glucocorticoid-Inducible Vascular Permeability Inhibitory Protein," pages 270–277 (January 1986)

34. Thompson et al, *Dis. Colon Rectum*, Vol. 29, No. 12, "Urinary Polyamines in Colorectal Cancer," pages 873–877 (December 1986)

35. Kovach et al, *Cancer Treat. Rep.*, Vol. 69, No. 1, "Enhancement of the Antiproliferative Activity of Human Interferon by Polyamine Depletion," pages 97–103 (January 1985)

36. Ferrante, *Immunology*, Vol. 54, No. 4, "Inhibition of Human Neutrophil Locomotion by the Polyamine Oxidase-Polyamine System," pages 785–790 (April 1985)

37. Oyanagui, *Agents Actions*, Vol. 14, No. 2, "Anti-Inflammatory Effects of Polyamines in Serotonin and Carrageenan Paw Edemata—Possible Mechanism to Increase Vascular Permeability Inhibitory Protein Level which is Regulated by Glucocorticoids and Superoxide Radical," pages 228–237 (February 1984)

38. Takigawa et al, *Cancer Res.*, Vol. 43, No. 8, "Inhibition of Mouse Skin Tumor Promotion and of Promoter-Stimulated Epidermal Polyamine Biosynthesis by Alpha-Difluoro-methylornithine," pages 3732–3738 (August 1983)

39. Slaga, *IARC Sci. Publ.*, No. 51, "Host Factors in the Susceptibility of Mice to Tumour Initiating and Promoting Agents," pages 257–273 (1983)

40. Bird et al, *Agents Actions*, Vol. 13, No. 4, "Putrescine—A Potent Endogenous Anti-Inflammatory Substance in Inflammatory Exudates," pages 342–347 (June 1983)

41. Ginsburg et al, *Inflammation*, "Effect of Leukocyte Hydrolases on Bacteria XVI. Activation by Leukocyte Factors and Cationic Substances of Autolytic Enzymes in Staphylococcus Aureus: Modulation by Anionic Polyelectrolytes in Relation to Survival of Bacteria in Inflammatory Exudates", pages 269–284 (September 1982)

42. Levine et al, *Am. J. Pathol.*, Vol. 107, No. 2, "Localization of Toxic Encephalopathies Near Lesions of Experimental Allergic Encephalomyelities," pages 135–141 (May 1982)

43. Clark et al, *Neurosci. Biobehav. Rev.*, Vol. 5, No. 1, "Changes in Body Temperature After Administration of Antipyretics, LSD, Delta 9-THC, CNS Depressants and Stimulants, Hormones, Inorganic Ions, Gases, 2,4-DNP and Miscellaneous Agents," pages 1–136 (Spring 1981)

44. Lanz et al, *Biochem. J.*, Vol. 194, No. 3, "Dissociation of Tumour-Promoter-Induced Effects on Prostaglandin Release, Polyamine Synthesis and Cell Proliferation of 3T3 Cells," pages 975–982 (March 1981)

45. Lowe, *J. Invest. Dermatol.,* Vol. 77, No. 1, "Ultraviolet Light and Epidermal Polyamines," pages 147–153 (July 1981)

46. Slaga et al, *Curr. Probl. Dermatol.,* Vol. 10, "Multistage Chemical Carcinogenesis in Mouse Skin," pages 193–218 (1980)

47. Weeks et al, *Biochem. Biophys. Res. Commun.*, Vol. 91, No. 4, "Inhibition of Phorbol Ester-Induced Polyamine Accumulation in Mouse Epidermis by Anti-Inflammatory Steroid," pages 1488–1496 (December 1979)

48. Allison et al, *Agents Actions,* Vol. 81, Nos. 1–2, "The Role of Macrophage Activation in Chronic Inflammation," pages 27–35 (January 1978)

49. Evans et al, *Blood,* Vol. 51, No. 6, "Polyamine Synthesis in Bone Marrow Granulocytes: Effect of Cell Maturity and Early Changes Following an Inflammatory Stimulus," pages 1021–1029 (June 1978)

50. Lichti et al, *Proc. Natl. Acad. Sci. USA*, Vol. 74, No. 9, "Dissociation of Tumor Promoter-Stimulated Ornithine Decarboxylase Activity and DNA Synthesis in Mouse Epidermis In Vivo and In Vitro by Fluocinolone Acetonide, a Tumor-Promotion Inhibitor," pages 3908–3912 (September 1977)

51. Giroud et al, *Therapie,* Vol. 27, No. 2, "Relations Entre les Proprietes Anti-inflammatoires et Anti-complementaires du Sulfate de Protamine et du Bromure D'hexadimethrine," [Relation Between the Anti-Inflammatory and Anti-Complementary Properties of Protamine Sulfate and Hexadimethrine Bromide], pages 297–307 (March–April 1972) (French language document)

52. Mitchell et al, *Br. J. Exp. Pathol.,* Vol. 52, No. 2, "The Electrophoretic Mobility of BP8 Ascites Tumour Cells and Allergized Lymph-Node Cells After Treatment with Inflammatory Mediators, Ptomaines, Polyamines, Antisera and Neuraminidase or Heparin," pages 152–171 (April 1971)

53. Mitchell et al, *J. Pathol.,* Vol. 103, No. 2, "The Effects of Inflammatory Mediators, Polyamines, Antisera, Neuraminidase and Heparin on the Cell-Surface Charge of BP8 Tumour Cells and Allergised Lymph-Node Cells," pages xiv–xv (February 1971)

The use of the naturally occurring polyamine putrescine in combination with other agents has been reported in U.S. Pat. No. 5,180,743 as a method of treating rheumatoid arthritis.

The structure, synthesis and impact on certain polyamine biosynthetic enzymes of PIP[4,4,4] have been reported. See, e.g., Bergeron et al, *J. Med. Chem.,* Vol. 37, pages 3464–3476 (1994).

SUMMARY OF THE INVENTION

The above and other objects are realized by the present invention, one embodiment of which comprises a method for treating inflammation in a mammalian host suffering therefrom; the method comprising administering to the mammal an amount of a bicyclic polyamine or a salt thereof with a pharmaceutically acceptable acid sufficient to exert an anti-inflammatory activity in the mammal, the polyamine having the formula:

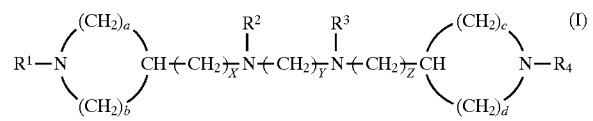

or a salt thereof with a pharmaceutically acceptable acid, wherein:

$R_1$, $R_2$, $R_3$ and $R_4$ may be the same or different and are hydrogen, straight- or branched-chain alkyl, aryl, aryl alkyl or cycloalkyl of 1 to 12 carbon atoms;

a, b, c and d may be the same or different and are integers from 0 to 8, except that when a or c is zero, b or d is greater than or equal to 3 and when a or c is one, b or d is greater than or equal to 2; and X, Y and Z may be the same or different; X and Z are integers from 0 to 10; and Y is an integer from 1 to 10, excluding the polyamine of the formula wherein a=b=c=d=2, X=Z=2 and Y=4.

Another embodiment of the invention relates to a pharmaceutical composition in unit dosage form for the treatment of inflammation in humans and non-human mammals suffering therefrom; the composition comprising an anti-inflammatory effective amount of a polyamine of Formula I or a salt thereof with a pharmaceutically acceptable acid and a pharmaceutically acceptable carrier therefor.

DETAILED DESCRIPTION OF THE INVENTION

The present invention is predicated on the discovery that bicyclic polyamines of the above formula, as well as acid salts thereof, exert an anti-inflammatory effect in humans and non-human mammals without certain toxic side effects associated with conventional anti-inflammatory agents. The active agents of the invention are particularly effective against the inflammation associated with arthritis. Other clinical indications include moderate pain, fever, dysmenorrhea, tendinitis/bursitis, sunburn, ankylosing spondylitis, psoriatic arthritis and Reiter's syndrome. They are also effective in preventing or treating inflammatory conditions requiring immunosuppression such as rheumatoid arthritis, systemic Lupus erythematosus, Hashimoto's thyroiditis, multiple sclerosis, Myasthenia gravis, Graves' disease, diabetes type I and uveitis, cutaneous manifestations of immunologically mediated illnesses such as Alopecia areata, and in treating inflammatory and hyperproliferative skin diseases such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne, and in situations of organ or tissue transplantation and graft-versus-host disease such as following bone marrow grafts.

The methods and compounds of the invention advantageously find use in ameliorating the mild to moderate pain and tenderness that often accompany inflammation. They are also effective in the control of moderate pain resulting from various musculoskeletal disorders, menstrual cramps and post-operative discomfort. A further advantage of the methods and compositions of the present invention resides in the fact that the bicyclic polyamine are orally active. Oral availability allows administration by mouth and renders the present invention particularly suitable for use in treating conditions involving chronic inflammation such as arthritis.

In the polyamines of the invention as described in Formula I, $R_1$–$R_4$ may be hydrogen, straight- or branched-chain alkyl, for example, methyl, ethyl, n-propyl, isopropyl, n-butyl, isobutyl, sec-butyl, tert-butyl and the like; aryl, for example, phenyl, p-tolyl, 2,4,6-trimethylphenyl and the like; aryl alkyl, for example, benzyl, $\alpha$-phenethyl, $\beta$-phenethyl and the like; cycloalkyl, for example, cyclohexyl, cyclobutyl, cyclopentyl, cycloheptyl and the like.

Figure 1:
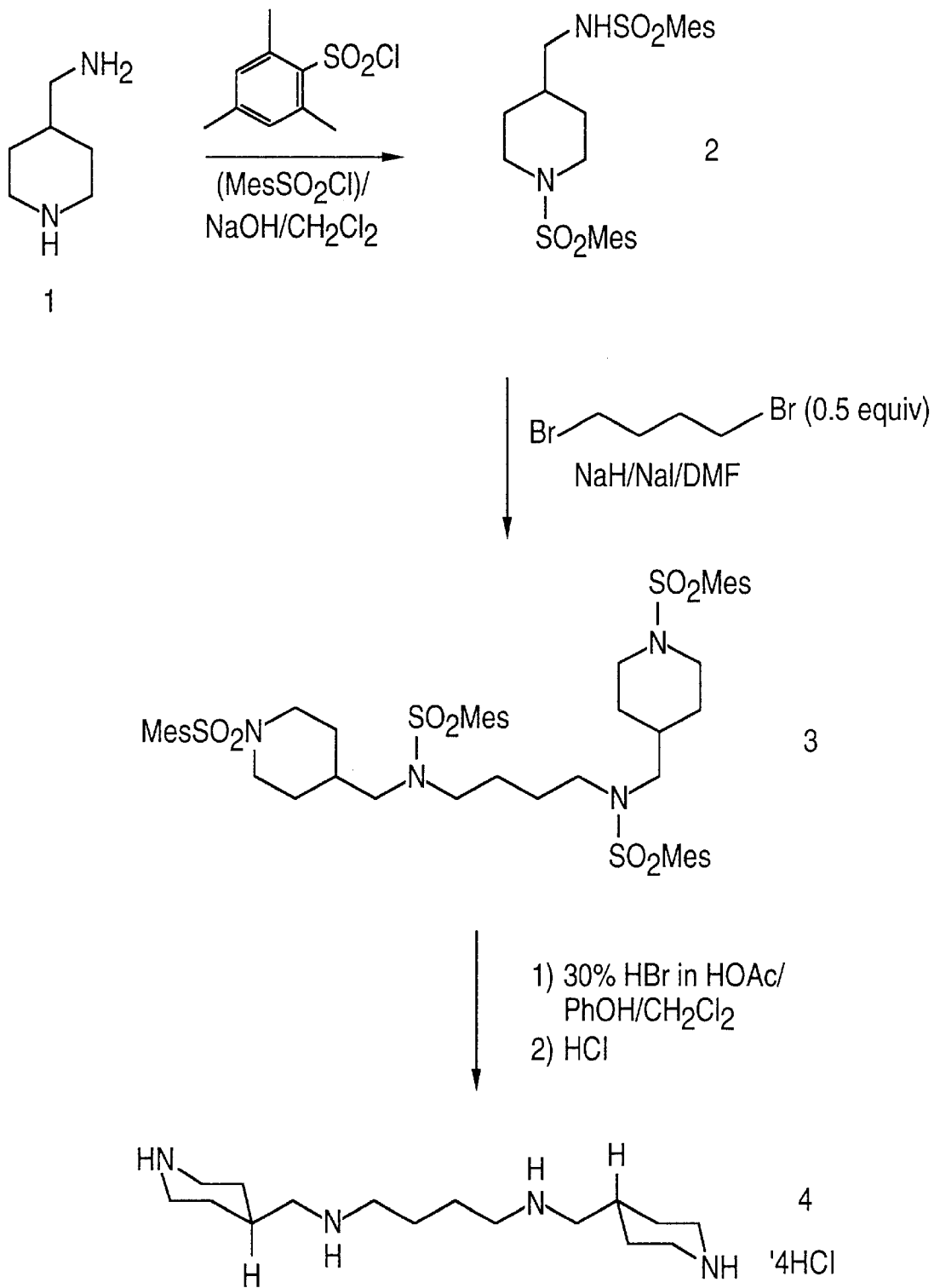
FIGS. 1–3 depict reaction schemes for preparing various bicyclic polyamines of the invention and intermediates therefor.
Figure 2:
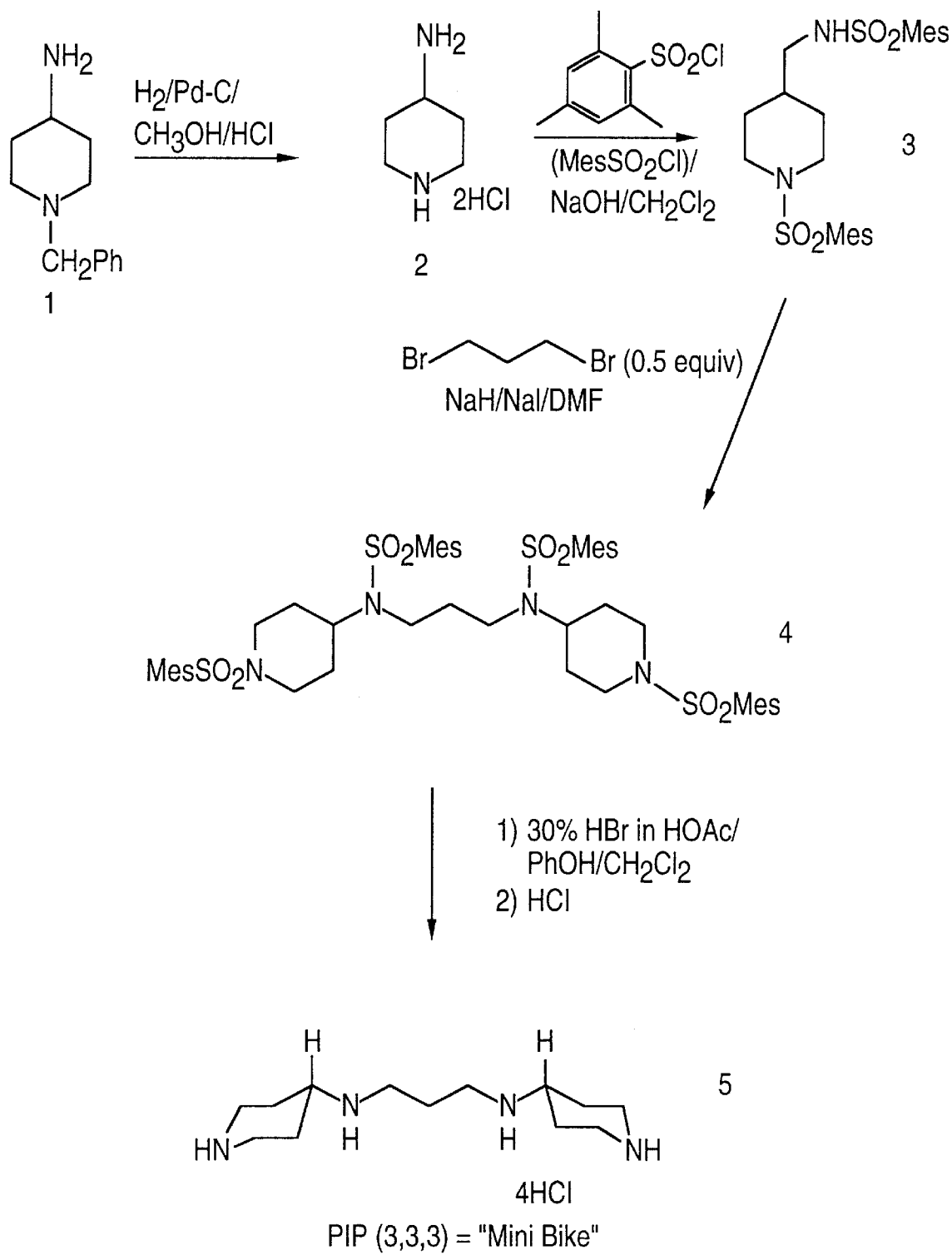
Figure 3:
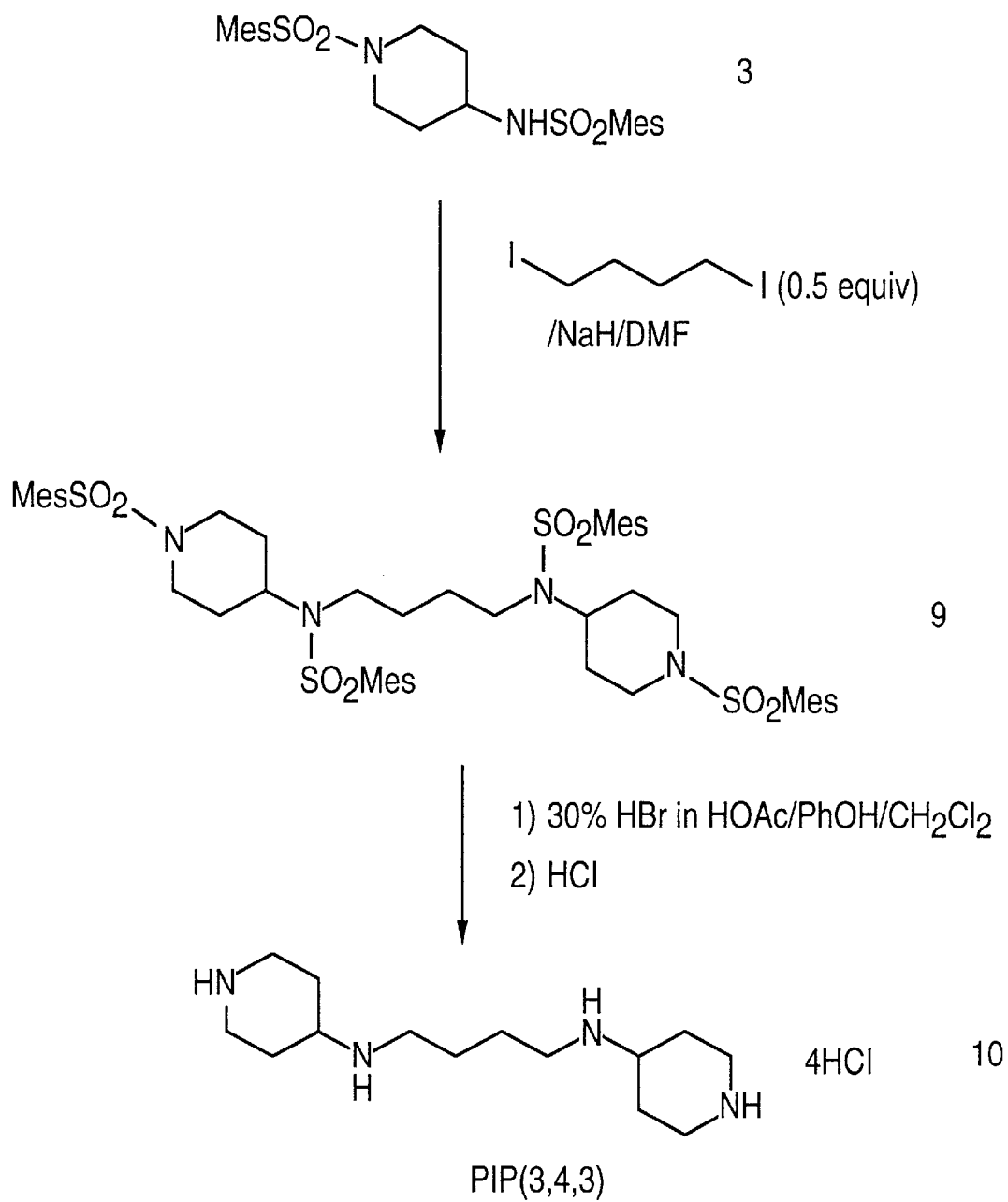
Figure 4A:
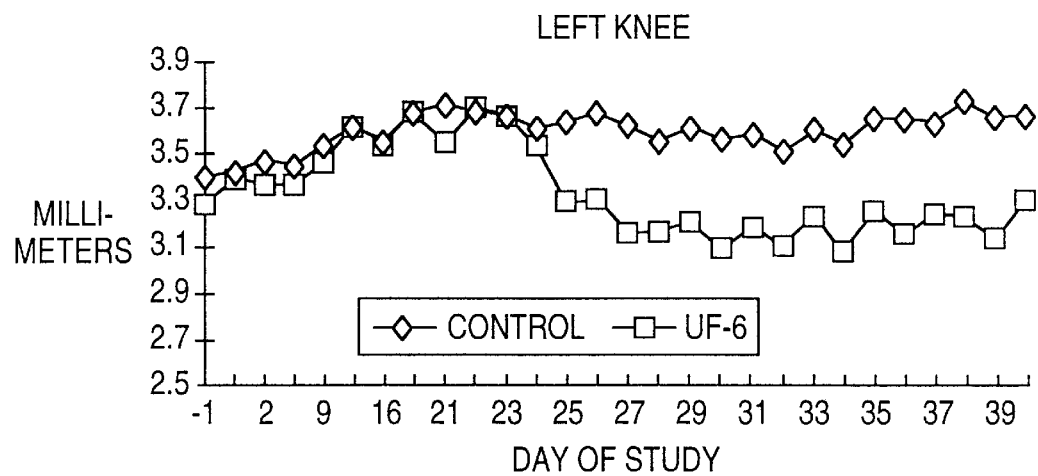
FIGS. 4–8 depict the results of an experiment in which the effect of PIP[4,4,4] on the prevention of type II collagen-induced arthritis in mice was measured. The degree of inflammation induced by type II collagen injections in mice treated with PIP[4,4,4] was significantly less than that in mice treated with equal volumes of saline (control) as monitored by measurement of various joints. Size of joints in milliliters is plotted against the study day for left and right knees (FIG. 4), left and right forelimb paws (FIG. 5), left and right forelimb elbows (FIG. 6), left and right hindlimb paws (FIG. 7), and left and right hindlimb ankle (FIG. 8).
Figure 4B:
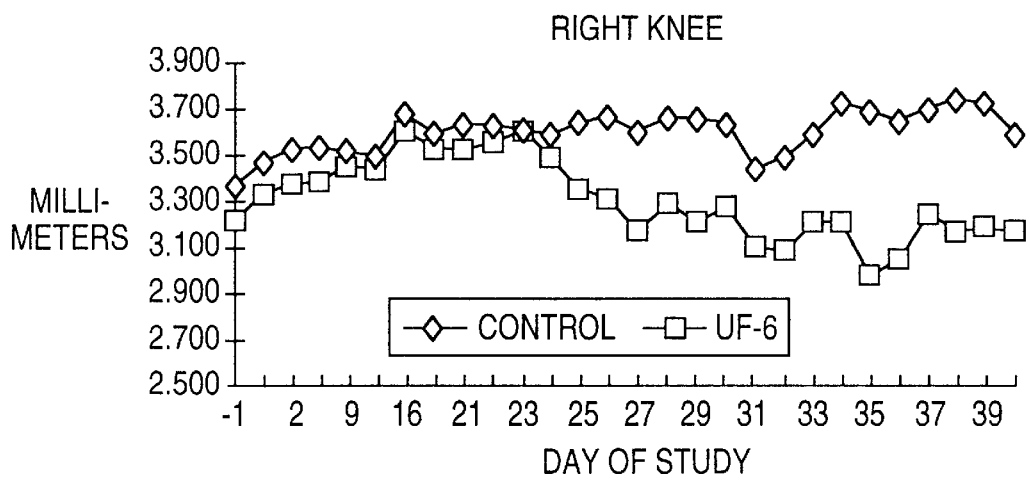
Figure 5A:
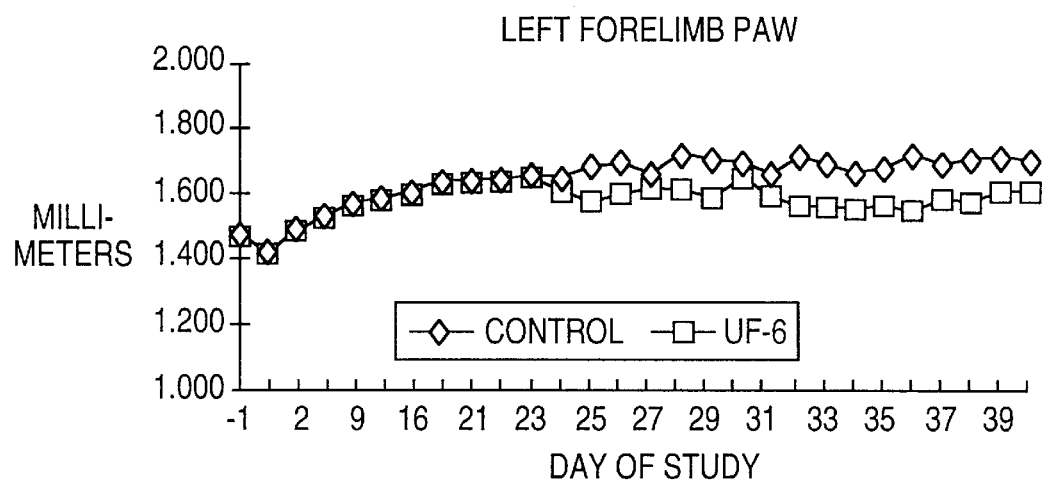
Figure 5B:
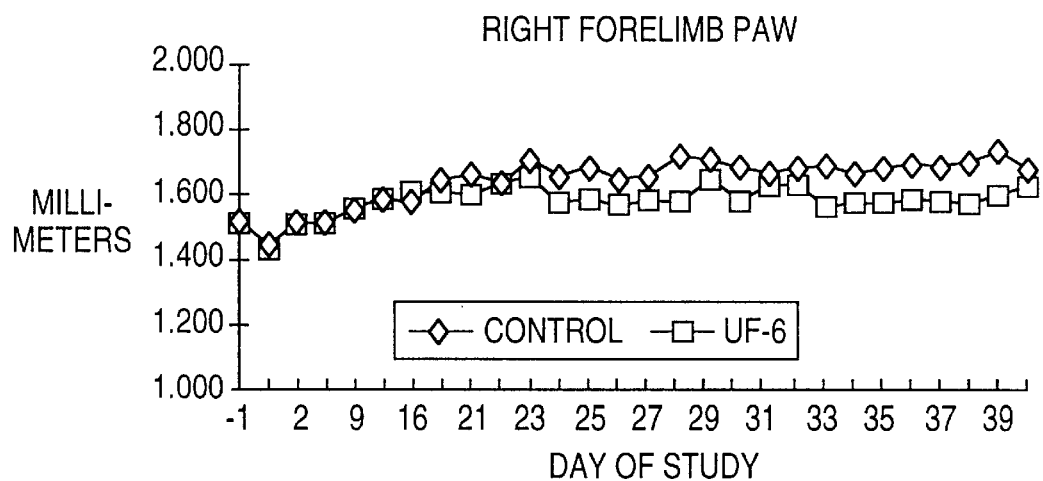
Figure 6A:
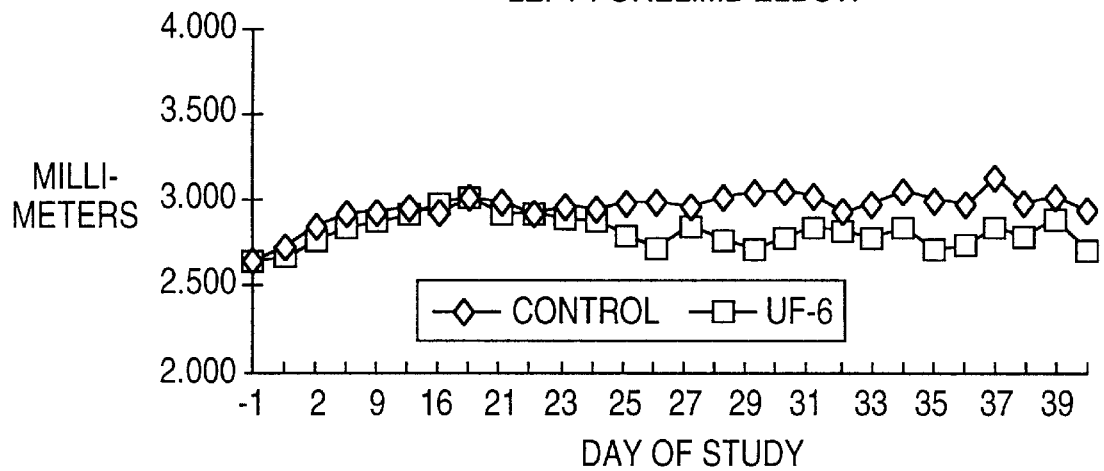
Figure 6B:
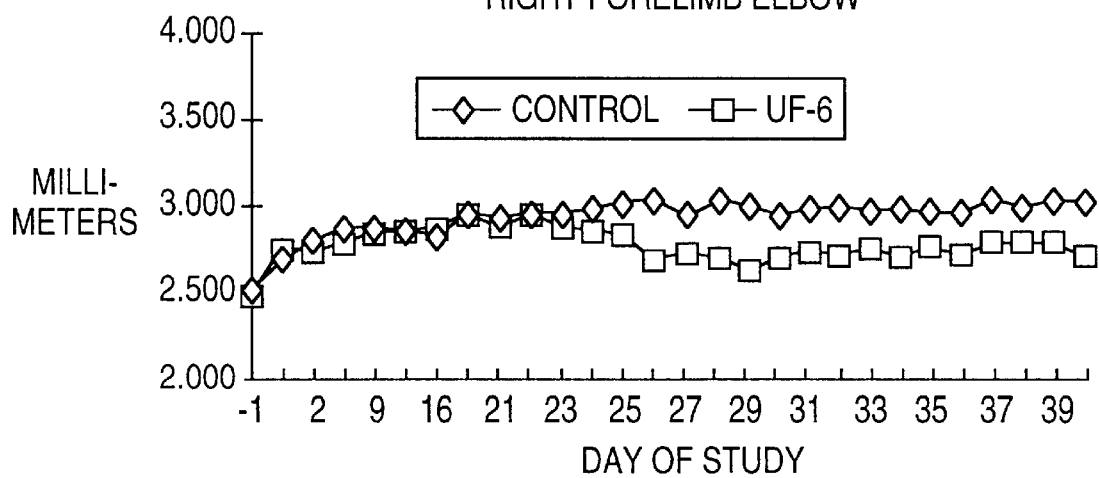
Figure 7A:
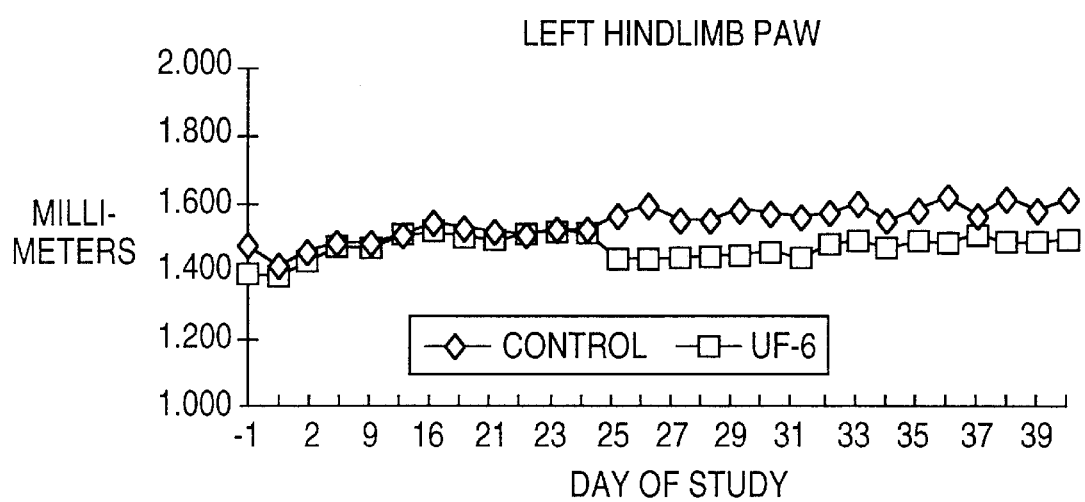
Figure 7B:
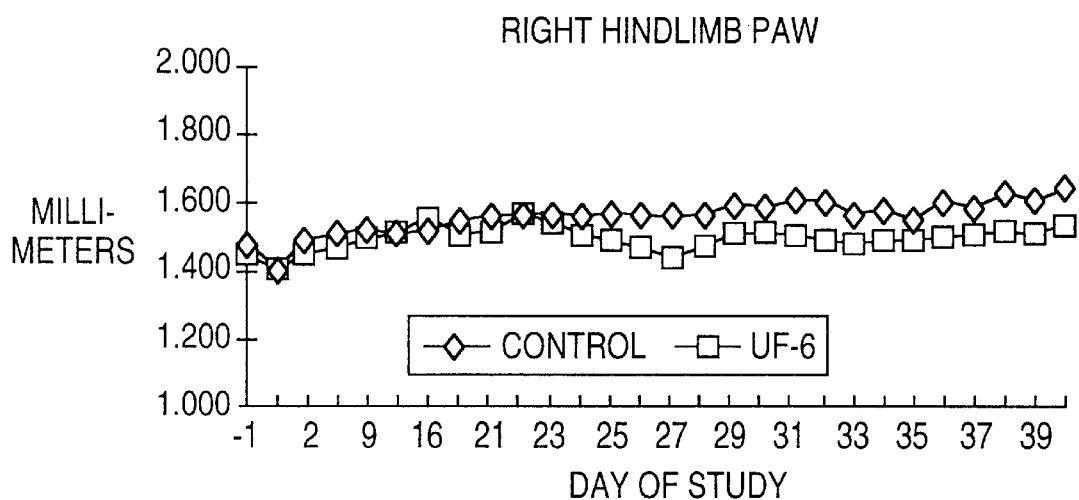

Particularly preferred polyamines are N,N'-Bis(4-piperidinylmethyl)-1,4-butanediamine (PIP[4,4,4]) [(4) FIG. 1], N,N'-Bis(4-piperidinyl)-1,3-propanediamine (PIP[3,3,3]) [(5) FIG. 2] and N,N'-Bis(4-piperidinyl)-1,4-butanediamine (PIP[3,4,3]) [(10) FIG. 3].

Compounds of the above formulae are synthesized according to the methods described in application Ser. No. 08/080,642 filed Jun. 22, 1993, the entire contents and disclosures of which are incorporated herein by reference.

Polyamines of Formula I in which the terminal nitrogens are incorporated into piperidine rings such as PIP[4,4,4], PIP[3,4,3] and PIP[3,3,3] may be preferably prepared using mesitylenesulfonyl-protected segments as shown in FIGS. 1–3. For example, a bicyclic polyamine (4 in FIG. 1) may be obtained by alkylation with 1,4-dibromobutane (0.5 equivalent)/NaH/DMF of the bis-sulfonamide (2) of 4-(aminomethyl)piperidine (1) to give (3). Reductive removal of the sulfonamide protecting groups with 30% HBr in HOAc/PhOH yields a bicyclic polyamine (4) (FIG. 1). As a further example (FIG. 2), the corresponding 3-3-3 bicyclic polyamine may be synthesized by alkylation of the appropriate mesitylenesulfonamide derivative (3), then deprotection with HBr as usual to give bicyclic spermine analogue (5). In an analogous fashion (FIG. 3), alkylation of mesitylenesulfonamide derivative (3) followed by deprotection of (9) gives the 3-4-3 bicyclic polyamine (10).

For the utility mentioned herein, the amount required of active agent, the frequency and mode of its administration will vary with the identity of the agent concerned and with the nature and severity of the condition being treated and is, of course, ultimately at the discretion of the responsible physician or veterinarian. In general, however, a suitable dose of agent for all of the above-described conditions will lie in the range of about 0.005 mg/kg to about 300 mg/kg, and preferably about 0.1 mg/kg to about 100 mg/kg, of mammal body weight being treated. The composition may be administered orally, topically or parenterally (intravenously, intradermally, intraperitoneally, intramuscularly or subcutaneously) for a period of time of from one to about thirty days. For chronic problems, the drug is administered as needed.

While it is possible for the agents to be administered as the raw substances, it is preferable to present them as a pharmaceutical formulation. The formulations of the present invention, both for veterinary and human use, comprise the agents together with one or more pharmaceutically acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible.

The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for oral administration may be in the form of discrete units such as capsules, cachets, tablets, or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active agent or dispensing agent. Molded tablets may be made by molding, in a suitable machine, a mixture of the powdered active ingredient and a suitable carrier moistened with an inert liquid diluent.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

Formulations suitable for topical administration include ointments, creams, gels and pastes. For example, the active agent may be conveniently prepared as a solution or stable emulsion with about 0.5% to about 10% by weight of the active agent with a compatible carrier. Suitable such carriers include oils such as cottonseed or linseed, waxes, paraffins, polyethylene glycol, silicones and the like. In addition to solutions or emulsions, micellar or liposomal formulations and the like may be used.

Formulations for oral, topical or parenteral administration may optionally contain one or more additional ingredients among which may be mentioned preservatives such as methyl hydroxybenzoate, chlorocresol, metacresol, phenol and benzalkonium chloride. Such materials are of special value when the formulations are presented in multi-dose containers.

Buffers may also be included to provide a suitable pH value for the formulation and suitable materials include sodium phosphate and acetate. Sodium chloride or other appropriate salts may be used to render a formulation isotonic with the blood. If desired, the formulation may be filled into the containers under an inert atmosphere such as nitrogen or may contain an anti-oxidant and are conveniently presented in unit dose or multi-dose form, for example, in a sealed ampoule.

It will be appreciated that while the agents described herein form acid addition salts and carboxylic acid salts, the biological activity thereof will reside in the agent itself. These salts may be used in human and in veterinary medicine and presented as pharmaceutical formulations in the manner and in the amounts (calculated as the base)

described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric and sulfuric acids; (b) organic acids: tartaric, acetic, citric, malic, lactic, fumaric, benzoic, glycollic, gluconic, gulonic, succinic and aryl-sulfonic, for example, p-toluenesulfonic and methanesulfonic acids.

The active agent or pharmaceutically acceptable derivatives or salts thereof may also be mixed with other pharmaceutically active materials that do not interfere with the desired action or with materials that enhance or supplement the desired action. Examples of appropriate other agents include antibiotics, antifungals, antivirals, antihistamines, immunosuppressants and other anti-inflammatory or analgesic compounds the like.

The invention is illustrated by the following non-limiting examples.

EXAMPLE 1

Preparation of PIP[4,4,4]

a. N,N'-Bis(2,4,6-trimethylbenzenesulfonyl)-4-(aminomethyl)-piperidine [(2) FIG. 1]—A solution of 2-mesitylenesulfonyl chloride (19.49 g, 89.1 mmol) in $CH_2Cl_2$ (100 ml) was added to 4-(aminomethylpiperidine) (1) (5.15 g, 45.1 mmol) in 1N NaOH (100 ml) at 0° C. After the addition was complete, the biphasic mixture was stirred for 24 hours (0° C. to room temperature). The layers were separated and the aqueous portion was extracted with $CHCl_3$ (2×). The combined organic phase was washed with 0.5N HCl (200 ml) and $H_2O$ (100 ml) dried with sodium sulfate and evaporated in vacuo. Recrystallization from aqueous ethanol produced 18.72 g (88%) of (2) as plates: mp 158.5°–160° C.; NMR ($CDCl_3$/TMS) δ0.8–2.0 (m, 5H), 2.25 (s, 6H), 2.46–2.93 (m+2s, 16H), 3.37–3.65 (m, 2H), 4.67 (t, 1H, J=6), 6.90 (s, 4H). Anal. calcd. for $C_{24}H_{34}N_2O_4S_2$: C, 60.22; H, 7.16; N, 5.85. Found: C, 60.31; H, 7.19; N, 5.86.

b. N,N'-1,4-Butanediylbis[2,4,6-trimethyl-N-[[1-[(2,4,6-trimethylphenyl)sulfonyl]-4-piperidinyl]methyl]-benzenesulfonamide [(3) FIG. 1]—Sodium hydride (80% in oil, 1.411 g, 47.0 mmol) was added to (2) (18.43 g, 38.5 mmol) and NaI (0.146 g, 0.97 mmol) in DMF (165 ml) at 0° C. The suspension was stirred for 1¾ hours at room temperature under nitrogen. 1,4-Dibromobutane (2.2 ml, 18.4 mmol) was added by syringe and the reaction mixture was heated at 84° C. for 19 hours. After cooling to 0° C., $H_2O$ (200 ml) was cautiously added to quench residual NaH, followed by extraction with $CHCl_3$ (300 ml, 2×100 ml). The combined organic phase was washed with 1% $Na_2SO_3$ (100 ml) and $H_2O$ (2×100 ml), dried with sodium sulfate and evaporated under high vacuum. Recrystallization from EtOAc/$CHCl_3$ gave 13.00 g (70%) of (3) as an amorphous solid: mp 202°–203.5° C.; NMR ($CDCl_3$/TMS) δ0.75–1.90 (m, 14H), 2.25 (s, 12H), 2.40–3.18 (m+2s, 36H), 3.3–3.6 (m, 4H) , 6.87 (s, 8H) . Anal. calcd. for $C_{52}H_{74}N_4O_8S_4$: C, 61.75; H, 7.37; N, 5.54. Found: C, 61.49; H, 7.39; N, 5.43.

c. N,N'-Bis(4-piperidinylmethyl)-1,4-butanediamine [(4) FIG.. 1]—30% HBr in acetic acid (100 ml) was added over 10 minutes to a solution of (3) (5.34 g, 5.28 mmol) and phenol (18.97 g, 0.202 mol) in $CH_2Cl_2$ (75 ml) at 0° C. The reaction was stirred for 24 hours (0° C. to room temperature) and cooled to 0° C. Distilled $H_2O$ (120 ml) was added, followed by extraction with $CH_2Cl_2$ (3×100 ml). The aqueous layer was evaporated under high vacuum. The residue was basified with 1N NaOH (12 mol) and 50% (w/w) NaOH (20 ml) with ice cooling, followed by extraction with $CHCl_3$ (10×50 ml), while adding NaCl to salt out the aqueous layer. Organic extracts were dried with sodium sulfate and evaporated. The residue was taken up in ethanol (200 ml), acidified with concentrated HCl (3.5 ml) and solvents were removed under vacuum. Tetrahydrochloride salt was recrystallized with 7% aqueous EtOH to furnish 1.318 g (58%) of (4) as a white solid. NMR ($D_2O$/TSP) δ1.19–2.23 (m, 14H), 2.8–3.6 (m, 16H). Anal. calcd. for $C_{16}H_{38}Cl_4N_4$: C, 44.87; H, 8.94; N, 13.08. Found: C, 44.77; H, 9.00; N, 13.00.

EXAMPLE 2

N,N'-Bis(4-piperidinyl)-1,3-propanediamine (PIP[3,3,3]) [(5) FIG. 2]

Using a method analogous to that described in Example 1 above, and with the substitution of 4-aminopiperidine dihydrochloride (2) for 4-(aminomethyl)piperidine and 1,3-dibromopropane for 1,4-dibromobutane as depicted in FIG. 2, N,N'-Bis(4-piperidinyl)-1,3-propanediamine (PIP[3,3,3]) was synthesized. Recrystallization from aqueous ethanol produced a white solid: $^1$H NMR ($D_2O$/TSP) δ1.66–2.00 (m, 4H), 2.02–2.16 (m, 2H), 2.40 (d, 4H, J=4.7), 3.12–3.30 (m, 8H), 3.51–3.63 (m, 6H). Anal. calcd. for $C_{13}H_{32}Cl_4N_4$: C, 40.43; H, 8.35; N, 14.51. Found: C, 40.51; H, 8.43; N, 14.41.

EXAMPLE 3

N,N'-Bis(4-piperidinyl)-1,4-butanediamine) (PIP[3,4,3]) [(10) FIG. 3]

Using a method analogous to that described in Example 1 above, N,N'-Bis(4-piperidinyl)-1,4-butanediamine (PIP[3,4,3]) was synthesized from bis(mesitylenesulfonyl)diamine (3) and 1,4-diiodobutane as depicted in FIG. 3. Recrystallization from aqueous ethanol produced a white solid: $^1$H NMR ($D_2O$/TSP) δ1.72–1.96 (m, 8H), 2.34–2.45 (m, 4H), 3.05–3.22 (m, 8H), 3.45–3.66 (m, 6H); HRMS (FAB, glycerol/trifluoroacetic acid matrix) calcd. for $C_{14}H_{30}N_4$ (free amine) 255.2549 (M+H), found 255.2543 (M+H). Anal. calcd. for $C_{14}H_{34}Cl_4N_4 \cdot H_2O$: C, 40.20; H, 8.68; N, 13.39. Found: C, 40.55; H, 8.34; N, 13.36.

EXAMPLE 4

Inhibition of Acute Inflammation and Modulation of Autoimmune-mediated Response by PIP[4,4,4]

PIP[4,4,4] was obtained as described above. Distilled water was used as the vehicle for in vivo testing. PIP[4,4,4] was completely soluble in the vehicle. Commercially obtained chemicals used were indomethacin and hydrocortisone (Sigma, St. Louis, Mo., U.S.A.), aspirin (Miles Labs., Elkart, IN, U.S.A.), carrageenan (Tokyo Kasei Industry Co., Ltd.), *Mycobacterium tuberculosis* (Difco Labs., Detroit, Mich., U.S.A.) and carboxymethyl-cellulose (Wako Pure Chemical Industries, Osaka, Japan). Doses of all compounds used were calculated on the basis of the weight of the salt.

In these studies, Long Evans derived rats (body weight from 130–160 g) from the Animal Center of National Taiwan University Medical College were used. The animals were housed in stainless steel cages (in inches: 22 length×18 width×6 height) with 10 rats per cage. The environment was maintained under controlled temperature (20°–24° C.) and humidity (40%–70%) with 12 hours light-dark cycles at least one week prior to use. Free access to standard laboratory chow (Taiwan Sugar Co.) and tap water was granted. All aspects of this work including housing, experimentation and disposal of animals were performed in general accordance with the International Guiding Principles for Biomedical Research Involving Animals (CIOMS Publication No. ISBN 92 90360194, 1985).

a. Inhibition of acute inflammation—Inhibition of acute inflammation was measured using the carrageenan-induced paw edema model of Winter et al [*Proc. Soc. Exp. Biol. Med.*, Vol. 111, "Carrageenan-Induced Edema in Hind Paw of the Rat as an Assay for Anti-Inflammatory Drugs," pages 544–547 (1962)]. Test substances were administered, p.o. or i.p., to groups of 3 fasted rats one hour (or 30 minutes for i.p. treatment) before intraplantar injection of carrageenan (0.1 ml, 1% suspension) into the right hind paw. Paw swelling, measured by water displacement, was recorded 3 hours after carrageenan administration. Inhibition by more than 30% compared to vehicle-treated controls indicates significant activity.

PIP[4,4,4] exhibited acute anti-inflammatory activity by significantly reducing the extent of carrageenan-induced paw edema in rats at a dose of 30 mg/kg intraperitoneally (Table 1). This activity compared favorably with that seen with concurrently assessed aspirin (150 mg/kg p.o.) and hydrocortisone (25 mg/kg p.o.).

TABLE 1

INHIBITION OF CARRAGEENAN-INDUCED EDEMA IN RAT PAW BY ANTI-INFLAMMATORY DRUGS AND PIP[4,4,4]

| COMPOUND | ROUTE | DOSE (MG/KG) | PAW VOLUME (× 0.01 ML) | % EDEMA INHIBITION |
|---|---|---|---|---|
| Control (Dist. H$_2$O) | PO | — | 89<br>87<br>89<br>$\bar{X} = 88$ | 100 |
| Aspirin | PO | 150 | 54<br>47<br>43<br>$\bar{X} = 48$ | (46) |
| Hydrocortisone | PO | 25 | 56<br>63<br>60<br>$\bar{X} = 60$ | (32) |
| PIP[4,4,4] | IP | 30 | 32<br>40<br>39<br>$\bar{X} = 37$ | (58) | b. Modulation of immune-mediated inflammatory response—Modulation of immune-mediated inflammatory response in rats was measured using the adjuvant-induced arthritis model of Winter et al [*Arthritis Rheum.*, Vol. 9, "Treatment of Adjuvant Arthritis in Rats with Anti-Inflammatory Drugs," pages 394–404 (1966)]. Groups of 5 male rats (weighing from 130–150 g) were used. A finely ground suspension of 0.3 mg/killed *Mycobacterium tuberculosis* in 0.1 ml of light mineral oil (Complete Freund's Adjuvant, CFA) was administered into the subplantar region of the right hind paw on Day 1. Hind paw volumes were measured by water displacement on Days 0, 1, 5, 14 and 18. Test substances were dissolved or suspended in 0.5% carboxymethyl-cellulose and administered orally on 5 consecutive days from Day 1 through Day 5. A concurrent vehicle control group was used to eliminate the generally minor influence of animal handling (stress-induced adrenal stimulation). Two concurrent active reference agent groups served to validate the assay system. The percent inhibitions of swelling in the injected and uninjected paws of the control and treated groups were calculated as shown in the following formulae.

A. Day 1→Day 0: Percent inhibition on the first day of CFA injection and one dose of test substance:

$$\frac{[(VR1 - VR0) \text{ of control}] - [(VR1 - VR0) \text{ of test substance}]}{[(VR1 - VR0) \text{ of control}]} \times 100\%$$

B. Day 5→Day 0: Percent inhibition on the 5th day after 5 doses of test substance:

$$\frac{[(VR5 - VR0) \text{ of control}] - [(VR5 - VR0) \text{ of test substance}]}{[(VR5 - VR0) \text{ of control}]} \times 100\%$$

C. Day 5→Day 1: Percent inhibition of paw volume change between Day 1 and Day 5:

$$\frac{[(VR5 - VR1) \text{ of control}] - [(VR5 - VR1) \text{ of test substance}]}{[(VR5 - VR1) \text{ of control}]} \times 100\%$$

D. Day 14→Day 0: Percent inhibition of untreated paw on Day 14 relative to Day 0:

$$\frac{[(VL14 - VR0) \text{ of control}] - [(VL14 - VL0) \text{ of test substance}]}{[(VL14 - VR0) \text{ of control}]} \times 100\%$$

E. Day 18→Day 0: Percent inhibition of untreated paw on Day 18 relative to Day 0:

$$\frac{[(VL18 - VR0) \text{ of control}] - [(VL18 - VL0) \text{ of test substance}]}{[(VL18 - VR0) \text{ of control}]} \times 100\%$$

F. Day 18→Day 14: Percent inhibition of untreated paw volume change between Day 14 and Day 18:

$$\frac{[(VL18 - VL14) \text{ of control}] - [(VL18 - VL14) \text{ of test substance}]}{[(VL18 - VR14) \text{ of control}]} \times 100\%$$

Inhibition of paw swelling by greater than 30% was considered significant. Changes in body weight (Day 18 v. Day 0) were recorded and the presence (+) or absence (−) of polyarthritic in signs are also recorded on Day 19 in the experimental animals' paws (P), tails (T), noses (N) and ears (E).

As shown in Table 2, PIP[4,4,4] at a daily dose of 100 mg/kg p.o. for 5 consecutive days, reduced both part of the acute phase and inhibited the development of the late phase swelling in the contralateral paw. Similar to concurrently assessed hydrocortisone and indomethacin, PIP[4,4,4] did not affect weight gain reductions, compared to vehicle-treated animals during the course of the 18 day study. Unlike hydrocortisone and indomethacin, PIP[4,4,4] did not prevent the appearance of signs of polyarthritis in the paws of the rats.

TABLE 2

ADJUVANT ARTHRITIS TEST

| Compound | Route | Dose (mg/kg) | Net Swelling of Paw Volume (ml) and Inhibition Percentage | | | | | | B.W. Gain (g) | Polyarthritis | | | |
|---|---|---|---|---|---|---|---|---|---|---|---|---|---|
| | | | A (1-0) | B (5-0) | C (5-1) | D (14-0) | E (18-0) | F (18-14) | (18-0) | P | T | N | E |
| Vehicle (0.5% CMC) | PO | 10 ml/kg × 5 | 0.90 | 1.90 | 1.00 | 0.52 | 1.01 | 0.49 | 30 | + | – | – | – |
| " | PO | 10 ml/kg × 5 | 0.80 | 1.70 | 0.90 | 0.30 | 0.47 | 0.17 | 60 | + | – | – | – |
| " | PO | 10 ml/kg × 5 | 0.80 | 1.71 | 0.91 | 0.57 | 0.84 | 0.27 | 40 | + | – | – | – |
| " | PO | 10 ml/kg × 5 | 0.80 | 1.40 | 0.60 | 0.32 | 0.40 | 0.08 | 40 | + | – | – | – |
| " | PO | 10 ml/kg × 5 | 0.85 | 1.54 | 0.69 | 0.54 | 1.03 | 0.49 | 40 | + | – | – | – |
| Average | | | 0.83 | 1.65 | 0.82 | 0.45 | 0.75 | 0.30 | 42 | | | | |
| PIP[4,4,4] | PO | 100 × 5 | 0.83 | 1.17 | 0.34 | 0.25 | 0.35 | 0.10 | 20 | + | – | – | – |
| " | PO | 100 × 5 | 0.79 | 1.49 | 0.70 | 0.43 | 0.55 | 0.12 | 35 | + | – | – | – |
| " | PO | 100 × 5 | 0.70 | 1.04 | 0.34 | 0.23 | 0.37 | 0.14 | 35 | + | – | – | – |
| " | PO | 100 × 5 | 0.87 | 1.37 | 0.50 | 0.34 | 0.45 | 0.11 | 5 | + | – | – | – |
| " | PO | 100 × 5 | 0.51 | 1.03 | 0.52 | 0.20 | 0.53 | 0.33 | 30 | + | – | – | – |
| Average | | | 0.74 | 1.22 | 0.48 | 0.29 | 0.45 | 0.16 | 25 | | | | |
| Inhibition % | | | 11 | 26 | (41) | (36) | (40) | (47) | | | | | |
| Hydrocortisone | PO | 30 × 5 | 0.78 | 0.89 | 0.11 | 0.43 | 0.53 | 0.10 | 40 | + | – | – | – |
| " | PO | 30 × 5 | 0.65 | 0.96 | 0.31 | 0.31 | 0.38 | 0.07 | 30 | – | – | – | – |
| " | PO | 30 × 5 | 0.70 | 0.86 | 0.16 | 0.30 | 0.66 | 0.36 | 25 | – | – | – | – |
| " | PO | 30 × 5 | 0.82 | 0.98 | 0.16 | 0.38 | 0.72 | 0.34 | 20 | – | – | – | – |
| " | PO | 30 × 5 | 0.70 | 1.61 | 0.91 | 0.33 | 0.41 | 0.08 | 0 | – | – | – | – |
| Average | | | 0.73 | 1.06 | 0.33 | 0.35 | 0.54 | 0.19 | 23 | | | | |
| Inhibition % | | | 12 | (36) | (60) | 22 | 28 | (37) | | | | | |
| Indomethacin | PO | 5 × 5 | 0.53 | 0.84 | 0.31 | 0.20 | 0.43 | 0.23 | 10 | – | – | – | – |
| " | PO | 5 × 5 | 0.58 | 0.86 | 0.28 | 0.40 | 0.50 | 0.10 | 15 | – | – | – | – |
| " | PO | 5 × 5 | 0.58 | 0.72 | 0.14 | 0.26 | 0.51 | 0.25 | 5 | – | – | – | – |
| " | PO | 5 × 5 | 0.51 | 0.81 | 0.30 | 0.42 | 0.49 | 0.07 | 5 | – | – | – | – |
| " | PO | 5 × 5 | 0.45 | 1.02 | 0.57 | 0.12 | 0.22 | 0.10 | 5 | – | – | – | – |
| Average | | | 0.53 | 0.85 | 0.32 | 0.28 | 0.43 | 0.15 | 8 | | | | |
| Inhibition % | | | (36) | (48) | (61) | (38) | (43) | (50) | | | | | |

EXAMPLE 5

Effect of PIP[4,4,4] on B and T Cell Mitogenesis and the Mixed Lymphocyte Response This study examined the potential immunomodulatory activities of PIP[4,4,4] on mouse spleen cells using in vitro techniques. The effect of the compound on the ability of murine splenocytes to respond to the G cell mitogen concanavalin A (Con A) and the B cell mitogen lipopolysaccharide (LPS) was studied. These mitogens non-specifically activate lymphocytes to proliferate and are general indicators of what effect a compound has on T or B cell function. In addition, the compound was tested for its effect on the mixed lymphocyte response (MLR). The MLR is an in vitro manifestation of cell-mediated immunity in which T cells respond to differences in major histocompatibility complex (MHC) class II molecules (Ia antigens) expressed on foreign or allogeneic leukocytes (primarily B cells and microphages/monocytes).

PIP[4,4,4] (molecular weight 428.3) was obtained as a powder and was solubilized in medium. Controls included medium alone (100% of control), as well as various concentrations of cyclosporin A (CsA, a known immunosuppressant for these assays) and ethanol (EtOH, vehicle for CsA).

a. Preparation of cells—Under sterile conditions, spleens were removed from BALB/c ($H\text{-}2^d$) and CBA/J ($H\text{-}2^k$) mice. BALB/c splenocytes were used as responder cells in the mitogen assays and the MLR assays, whereas CBA/J cells were used as stimulator cells in the MLR assays. Single cell suspensions were prepared in complete medium (RPMI-1640 plus 10% fetal calf serum, 100 µg/ml streptomycin, 100 µg/l penicillin, 10 µg/ml gentamicin, 2 mM L-glutamine and $2 \times 10_5$M 2-mercaptoethanol). Cells were exposed to various concentrations of the test compounds for the entire culture period. The initial dilutions in medium were filter sterilized to maintain aseptic conditions.

b. Mitogen assays—Con A and LPS were obtained from Sigma Chemical Co. (St. Louis, Mo., U.S.A.). $2 \times 10^5$ BALB/c splenocytes were added per well. The final concentration of Con A used was 3 µg/ml which had been shown to be optimal for T cell stimulation in previous studies. The final concentration of LPS used was 25 µg/ml which had been shown to be optimal for stimulation in previous studies. Triplicate wells were set up in 96-well flat-bottom microtiter plates for all treated cultures and positive controls (100% of control) were performed in replicates of nine wells. Plates were incubated at 37° C. in a humidified $CO_2$ incubator for 3 days, pulsed with 1 µCi $^3$H-TdR/well for 6–16 hours, harvested and counted in a liquid scintillation counter. All data were processed using Lotus 1-2-3 and SigmaPlot software.

c. Mixed Lymphocyte Response (MLR)—Previous studies had demonstrated a vigorous proliferative response in a one-way MLR using BALB/c responders and CBA/J stimulators. Thus, a BALB/c ($2 \times 10^5$ cells/well) anti-CBA/J ($8 \times 10^5$ cells/well) MLR combination was used in these studies. CBA/J spleen cells were irradiated with 2,000 R to prevent them from responding to BALB/c MHC antigens. Triplicate wells were set up in 96-well flat-bottom microtiter plates for all treated cultures and positive controls (100% of control) were performed in replicates of nine wells. Plates were incubated at 37° C. in a humidified $CO_2$ incubator for 5 days, pulsed with 1 µCI $^3$H-Td3/well for 6–16 hours, harvested and counted in a liquid scintillation counter. All data were processed using Lotus 1-2-3 and SigmaPlot software.

d. Results—The results from one set of experiments are shown in Tables 3–5. The means +standard deviation (SD)

of the counts per minutes (cpm) indicating the proliferative responses of replicate wells are shown for the Con A (Table 3), LPS (Table 4) and MLR (Table 5) assays. Background responses (responders only) were low and within the laboratory historical range, indicating no significant pre-activation of the cells from their animal donors. All positive control responses (100% of control) were vigorous, indicating that the responder cells were responsive to the various stimuli.

A positive control compound, CsA, was used to demonstrate immunosuppression in these studies. As shown in Tables 3–5, CsA was immunosuppressive for all assays. Because CsA is dissolved in EtOH, corresponding concentrations of EtOH diluted in medium were included to control for any effects on the cells from the alcohol alone. In general, EtOH was not inhibitory at the concentrations tested in these assays as shown in Tables 3–5.

As shown in Table 3, PIP[4,4,4] had no inhibitory effect on the Con A response, suggesting no general effect on T cells.

As shown in Table 4, some inhibition of the LPS response was observed for PIP[4,4,4], suggesting some effects on B cell proliferation. There was some dose-dependent suppression caused by PIP[4,4,4] in the 1–100 μm range.

As shown in Table 5, the MLR was inhibited by PIP[4,4,4] primarily at 10 and 100 μm, suggesting inhibition of the proliferative response of $CD4^+$ T cells, the cells which respond to alloantigens. Alternatively, if the compound effected the expression of class II MHC (Ia) molecules on the stimulator cells, this may also account for these results.

TABLE 3

Mitogen Response to Con A

| Compound | Drug Concentration | Proliferative Response (CPM) Mean ± SD | % Control |
|---|---|---|---|
| Media (no Con A) | None | 1319 ± 352 | — |
| Media (positive control) | None | 196119 ± 22511 | 100 |
| CsA | 1.000 μm | 7916 ± 1139 | 4 |
|  | 0.100 μm | 30719 ± 4963 | 16 |
|  | 0.010 μm | 54539 ± 5810 | 28 |
|  | 0.001 μm | 96868 ± 22376 | 50 |
| EtOH | 0.013000% | 277029 ± 23757 | 140 |
|  | 0.001300% | 290003 ± 20210 | 146 |
|  | 0.000130% | 296690 ± 28125 | 151 |
|  | 0.000013% | 238348 ± 17009 | 120 |
| PIP[4,4,4] | 1000.000 μm | 273418 ± 14954 | 138 |
|  | 100.000 μm | 313504 ± 279 | 158 |
|  | 10.000 μm | 365771 ± 2876 | 185 |
|  | 1.000 μm | 340397 ± 25586 | 172 |
|  | 0.100 μm | 333419 ± 31211 | 168 |
|  | 0.010 μm | 343389 ± 21927 | 173 |

TABLE 4

Mitogen Response to LPS

| Compound | Drug Concentration | Proliferative Response (CPM) Mean ± SD | % Control |
|---|---|---|---|
| Media (no LPS) | None | 1983 ± 306 | — |
| Media (positive control) | None | 176092 ± 20673 | 100 |
| CsA | 1.000 μm | 25054 ± 4947 | 14 |
|  | 0.100 μm | 79687 ± 3818 | 45 |
|  | 0.010 μm | 81281 ± 213033 | 46 |
|  | 0.001 μm | 133300 ± 6182 | 76 |

TABLE 4-continued

Mitogen Response to LPS

| Compound | Drug Concentration | Proliferative Response (CPM) Mean ± SD | % Control |
|---|---|---|---|
| EtOH | 0.013000% | 169245 ± 11996 | 96 |
|  | 0.001300% | 162318 ± 7643 | 92 |
|  | 0.000130% | 162300 ± 34911 | 92 |
|  | 0.000013% | 162784 ± 7406 | 92 |
| PIP[4,4,4] | 1000.000 μm | 83427 ± 18281 | 47 |
|  | 100.000 μm | 117804 ± 14014 | 67 |
|  | 10.000 μm | 187500 ± 8089 | 106 |
|  | 1.000 μm | 192921 ± 32628 | 110 |
|  | 0.100 μm | 174197 ± 23886 | 99 |
|  | 0.010 μm | 175516 ± 10793 | 100 |

TABLE 5

Mixed Lymphocyte Response

| Compound | Drug Concentration | Proliferative Response (CPM) Mean ± SD | % Control |
|---|---|---|---|
| Media (no stimulators) | None | 1065 ± 314 | — |
| Media (with stimulators; positive control) | None | 41679 ± 2791 | 100 |
| CsA | 1.000 μm | 355 ± 30 | 1 |
|  | 0.100 μm | 558 ± 42 | 1 |
|  | 0.010 μm | 13969 ± 3280 | 34 |
|  | 0.001 μm | 26629 ± 9391 | 64 |
| EtOH | 0.013000% | 30099 ± 8116 | 72 |
|  | 0.001300% | 37528 ± 7203 | 90 |
|  | 0.000130% | 34064 ± 1054 | 82 |
|  | 0.000013% | 38955 ± 14703 | 93 |
| PIP[4,4,4] | 1000.000 μm | 22583 ± 2490 | 54 |
|  | 100.000 μm | 29717 ± 3146 | 71 |
|  | 10.000 μm | 568531 ± 6200 | 136 |
|  | 1.000 μm | 54594 ± 11873 | 131 |
|  | 0.100 μm | 411919 ± 6106 | 99 |
|  | 0.010 μm | 330859 ± 11640 | 79 |

EXAMPLE 6

Prevention Of Type II Collagen-Induced Arthritis In Mice By PIP[4,4,4]

The purpose of this study was to test PIP[4,4,4] in an experimental model of arthritis in DBA/1J mice by observing the onset, duration and remission of inflammation utilizing type II collagen. Twenty male DBA/1J mice, equally divided into two groups of ten animals, were immunized with a single intradermal injection of native type II chick collagen (100 μg/animal, intradermally) in Complete Freund's Adjuvant (CFA) on Day 0. Beginning on Day 20, one group was injected daily i.p. with 75 mg/kg PIP[4,4,4]; the other group received an equal volume (7.5 ml/kg) of isotonic saline i.p. as a comparable control group. On Day 21, both groups received a challenge dose of type II collagen (100 μg/animal, intradermally at the base of the tail, in 50 μl CFA). Daily joint measurements were recorded once per day on Days 20–40. Joints were measured using a constant tension caliper (Mitutoyo Digimatic Thickness Gauge). All mice were measured before the start of the study (Day −1) to obtain baseline readings at three joints on the right and left hindlimb (paw thickness, ankle width and knee width) and two joints of the right and left forelimb (paw thickness and elbow width). On Day 26 of the study, five days following initiation of PIP[4,4,4] treatment, the dosage was decreased from 75 to 50 mg/kg due to overt toxicity of compound administration. Four of ten mice treated with PIP[4,4,4] died or were sacrificed in extremis, during the treatment period.

Figure 8A:
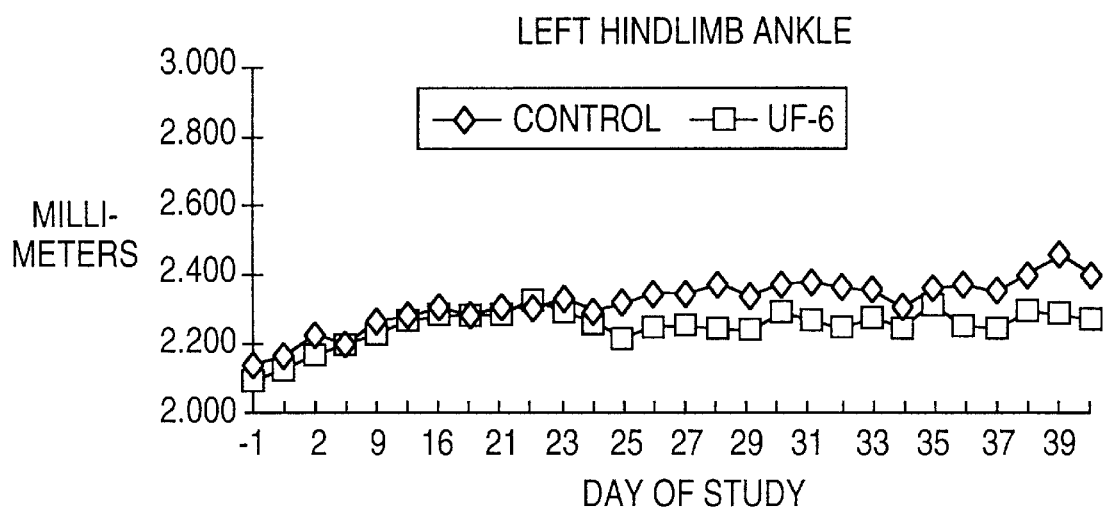
Figure 8B:
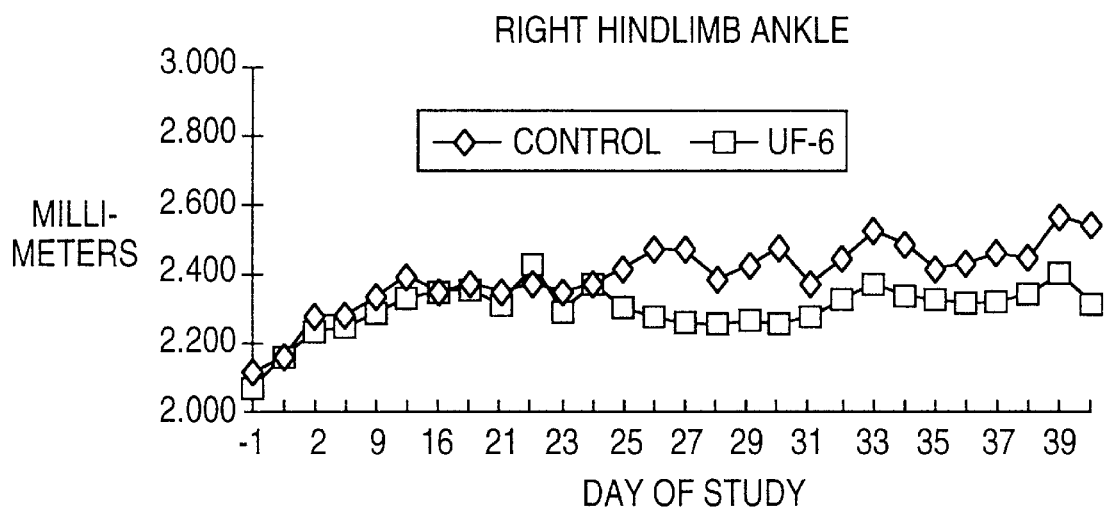

Joint measurements decreased in mice treated with PIP [4,4,4] as compared to untreated control mice. This effect was first evident by Day 25 of the study, five days following initiation of PIP[4,4,4] treatment. FIGS. 4–8 show the joint measurement data: the size of the various joints in millimeters for PIP[4,4,4] and control mice is plotted against the study day for left and right knee (FIG. 4), left and right forelimb paw (FIG. 5), left and right forelimb elbow (FIG. 6), left and right hindlimb paw (FIG. 7) and left and right hindlimb ankle (FIG. 8).

EXAMPLE 7

Analgesic Activity Of PIP[4,4,4]

The method of Siegmund et al [*Proc. Soc. Exp. Biol. Med.*, Vol. 95, pages 729–731 (1957)] was used to measure the analgesic activity of PIP[4,4,4]. Groups of 10 male ICR mice weighing 22±2 g were employed. Various doses of test compound, dissolved in a vehicle of distilled water, were administered intraperitoneally. The control group received vehicle alone. At 30 minutes post dosing, 2 mg/kg of phenylquinone (P.Q.) was injected i.p. and the number of writhes exhibited during the following 5–10 minute period post P.Q. injection were recorded. The mean±SEM number of writhes in each treatment group was calculated and unpaired Student's t test was applied for comparison between vehicle and treated groups. Differences were considered significant when $P<0.05$. As shown in Table 6, PIP[4,4,4] exhibited analgesic activity as compared with the vehicle control.

TABLE 6

Analgesia (P.O. Writhing)

| COMPOUND | ROUTE | DOSE | (# WRITHES) (X ± SEM) | % INHIBITION |
|---|---|---|---|---|
| Vehicle | IP | 20 ml/kg | 14 ± 1 | |
| PIP[4,4,4] | IP | 100 mg/kg | 3 ± 1** | (79) |

**$P < 0.01$

EXAMPLE 8

Modulation Of Immune-Mediated Inflammatory Response

Modulation of immune-mediated inflammatory response in rats was measured using the adjuvant-induced arthritis model of Winter et al, *Arthritis Rheum.*, supra. Two separate studies utilizing this model were conducted as follows:

a. CFA was made by emulsifying 10 mg desiccated, ground *Mycobacterium tuberculosis* (H37Ra) in 15 ml heavy white mineral oil and 1 ml of saline.

Four groups consisting of 6 male Lewis rats weighing 150–200 g were injected subcutaneously at the base of the tail with 0.1 ml of CFA. Drugs to be assayed were administered 5 days beginning on the day of the adjuvant injection. The paw volume of the right and left rear paw of each rat were measured on the day of adjuvant injection and at regular intervals for 30 days thereafter.

b. CFA was made as in a. above. The emulsion was injected subcutaneously at the base of the tail and induced the arthritic state. Measurements of paw volume were made for 30 days to monitor paw swelling. Drug treatment began on Day 0.

Four groups consisting of 10 male Lewis rats weighing 150–200 g were injected subcutaneously at the base of the tail with 0.1 ml of CFA. Drugs to be assayed were administered for 5 days beginning on the day of the adjuvant injection.

The data was standardized between the two studies.

The control values from the two studies were averaged to give the fairest representation of the data. The results are set forth in Table 7 below.

TABLE 7

| COMPOUND | ROUTE | DOSE MG/KG | INITIAL DAY 14–0 | FINAL DAY 28–0 | % FINAL INHIBITION |
|---|---|---|---|---|---|
| Control | PO | | 1.16 | 1.91 | — |
| DiPIP[3,4,3] | PO | 100 | .391 | .571 | 70 |
| DiPIP[3,4,3] | PO | 100 | .709 | 1.12 | 41 |
| DiPIP[4,4,4] | PO | 100 | .496 | .801 | 58 |
| DiPIP[5,4,5] | PO | 100 | 1.24 | 1.72 | 9 |
| Voltaren | PO | 6 | .232 | .629 | 67 |
| Indomethacin | PO | 6 | .004 | 0.14 | 93 |

Unless defined otherwise, all technical and scientific terms used herein have the same meaning as commonly understood by one of ordinary skill in the art to which this invention belongs.

It is understood that the examples and embodiments described herein are for illustrative purposes only and that various modifications or changes in light thereof will be suggested to persons skilled in the art and are to be included within the scope of the application and the appended claims.

I claim:

1. A method for treating inflammation in a human or non-human mammal suffering therefrom comprising administering to said mammal an amount of a polyamine or a pharmaceutically acceptable acid salt thereof sufficient to exert an anti-inflammatory activity in said mammal, said polyamine having the formula:

$$R^1-N\begin{pmatrix}(CH_2)_a\\(CH_2)_b\end{pmatrix}CH(CH_2)_{\overline{X}}N(CH_2)_{\overline{Y}}N(CH_2)_{\overline{Z}}CH\begin{pmatrix}(CH_2)_c\\(CH_2)_d\end{pmatrix}N-R_4$$

with $R^2$ and $R^3$ on the central nitrogens, or a salt thereof with a pharmaceutically acceptable acid wherein:

$R_1$, $R_2$, $R_3$ and $R_4$ may be the same or different and represent H, straight- or branched-chain alkyl, aryl, aryl alkyl or cycloalkyl of 1–12 carbon atoms;

a, b, c and d may be the same or different and are integers from 0 to 8, except that when a or c is zero, b or d is greater than or equal to 3 and when a or c is one, b or d is greater than or equal to 2; and X, Y and Z may be the same or different; X and Z are integers from 0 to 10; and Y is an integer from 1 to 10, excluding the polyamine of the formula wherein $a=b=c=d=2$, $X=Z=2$ and $Y=4$.

2. The method of claim 1 wherein said inflammation is associated with arthritis.

3. The method of claim 1 wherein said polyamine is PIP[4,4,4], PIP[3,4,3] or PIP[3,3,3].

4. The method of claim 1 wherein said amount is from about 0.005 mg/kg to about 300 mg/kg of body weight of said mammal.

* * * * *